(12) United States Patent
Robertson et al.

(10) Patent No.: US 7,383,837 B2
(45) Date of Patent: Jun. 10, 2008

(54) INHALATION DEVICE

(75) Inventors: Duncan Robertson, Ware (GB); George Robusti, Ware (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 95 days.

(21) Appl. No.: 10/362,699

(22) PCT Filed: Aug. 9, 2001

(86) PCT No.: PCT/EP01/09202

§ 371 (c)(1),
(2), (4) Date: Dec. 2, 2003

(87) PCT Pub. No.: WO02/17998

PCT Pub. Date: Mar. 7, 2002

(65) Prior Publication Data

US 2005/0028814 A1 Feb. 10, 2005

(30) Foreign Application Priority Data

Aug. 29, 2000 (GB) ................................. 0021024.5

(51) Int. Cl.
*A61M 11/00* (2006.01)
*A61M 15/00* (2006.01)
(52) U.S. Cl. .......................... 128/200.23; 128/200.17; 128/200.14; 128/203.15
(58) Field of Classification Search ........... 128/200.11, 128/200.12, 200.14, 200.17, 200.23, 203.15
See application file for complete search history.

(56) References Cited

U.S. PATENT DOCUMENTS

| 5,201,308 | A | * | 4/1993 | Newhouse | 128/203.15 |
|---|---|---|---|---|---|
| 5,392,768 | A | * | 2/1995 | Johansson et al. | 128/200.14 |
| 5,394,866 | A | * | 3/1995 | Ritson et al. | 128/200.14 |
| 5,469,750 | A | | 11/1995 | Lloyd et al. | |
| 5,520,166 | A | * | 5/1996 | Ritson et al. | 128/200.14 |
| 5,522,378 | A | * | 6/1996 | Ritson et al. | 128/200.14 |
| 5,622,162 | A | * | 4/1997 | Johansson et al. | 128/200.14 |
| 5,904,139 | A | | 5/1999 | Hauser | |
| 6,062,214 | A | * | 5/2000 | Howlett | 128/200.23 |
| 6,119,684 | A | * | 9/2000 | Nohl et al. | 128/200.14 |
| 6,131,566 | A | * | 10/2000 | Ashurst et al. | 128/200.14 |
| 6,131,569 | A | * | 10/2000 | Schuster | 128/200.24 |
| 6,343,602 | B1 | * | 2/2002 | Scheuch et al. | 128/203.15 |
| 6,536,429 | B1 | * | 3/2003 | Pavlov et al. | 128/203.26 |

* cited by examiner

*Primary Examiner*—Teena Mitchell
*Assistant Examiner*—Annette Dixon
(74) *Attorney, Agent, or Firm*—J. Michael Strickland

(57) ABSTRACT

According to the present invention there is provided an inhalation device for dispensing medicament comprising a body (150), the body being shaped for receipt of a medicament carrier (286); and an actuator (10) having a mouthpiece (20), the actuator being reversibly movable between a dispensing position and a storage position; wherein the body includes an air channel (253), and the actuator includes an air hole (225) such that the air channel communicates with the air hole when the actuator is in the dispensing position and the air channel and air hole do not communicate when the actuator is in the storage position.

Figure 1:
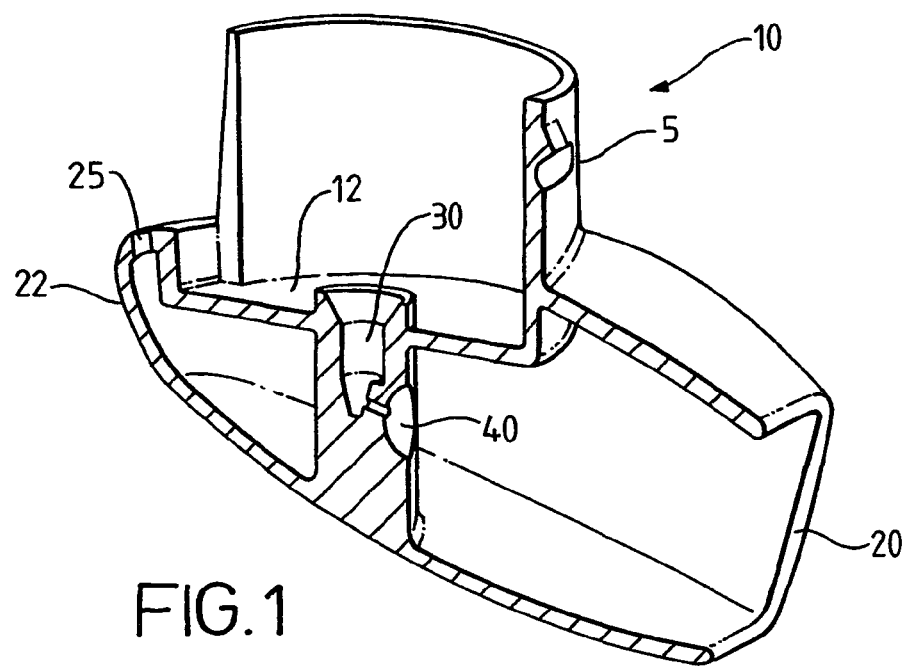

25 Claims, 4 Drawing Sheets

INHALATION DEVICE

This application is filed pursuant to 35 USC 371 as a U.S. National Phase Application of International Patent Application Ser. No. PCT/EP01/09202 filed 9 Aug. 2001, which claims priority from GB 0021024.5 filed on 29 Aug. 2000 in the United Kingdom.

FIELD OF THE INVENTION

The present invention relates to an inhalation device for use in the administration of medicament to a patient.

BACKGROUND TO THE INVENTION

The use of inhalation devices in the administration of medicaments, for example in bronchodilation therapy, is well known. Such devices generally comprise a body or housing within which a medicament container is located. A mouthpiece (or nozzle) is typically provided which communicates with the medicament container to allow passage of medicament from the source to the mouthpiece and thence, to the patient. When the patient breathes to take in the medicament, typically air is allowed to circulate throughout the body of the device to create airflow.

However, there are certain devices where it is advantageous that the volume of the body of the device that is exposed to airflow (and therefore moisture) is reduced. Typically such devices have moisture sensitive components such as medicament (for example dry powder) or electronic or other moisture sensitive equipment.

The applicants have now found that this problem can be salved by employing a device wherein the mouthpiece and the body of the device are separated such that the airflow between these parts is minimized. A specially created air hole in the mouthpiece and air channel in the body allow air to circulate through a part of the body not containing moisture sensitive components. These air holes and air channels are only able to communicate when the device is in a dispensing position. Preferably these air holes and channels are blocked during storage to prevent the entry of contaminants.

SUMMARY OF THE INVENTION

According to one aspect of the present invention there is provided an inhalation device for dispensing medicament comprising a body, said body being shaped for receipt of a medicament carrier; and an actuator having a mouthpiece, said actuator being reversibly movable between a dispensing position and a storage position;

wherein said body includes an air channel, and said actuator includes an air hole such that said air channel communicates with said air hole when the actuator is in said dispensing position and the air channel and air hole do not communicate when the actuator is in said storage position.

The term 'medicament carrier' is used in a general sense to mean any carrier for a medicament product which product can itself be in any suitable form e.g. aerosol, dry powder, solution etc. Suitable carriers include aerosol containers, blister packs, capsules and reservoirs.

Preferably the actuator additionally comprises a collar portion for receipt of a medicament carrier.

Preferably the actuator additionally includes a wall to create a closed off cavity around the mouthpiece such that air flow is between the air hole and mouthpiece only.

Preferably the actuator additionally comprises a support for a medicament carrier and nozzle providing communication between the mouthpiece and a medicament carrier inserted in said support.

Preferably either the air channel or air hole is blocked when the actuator is in the storage position. More preferably both the air channel and air hole are blocked when the actuator is in the storage position.

Preferably, the air channel is in the form of a slot.

Preferably the body has a plurality of air channels. Preferably said plurality of air channels are arranged in a finger arrangement. Alternatively said plurality of air channels are arranged in a series of grooves.

Preferably the mouthpiece has a plurality of air holes. In one embodiment of the invention the air hole is a slot.

Preferably the mouthpiece is covered by the body in the storage position and protrudes from the body in the dispensing position.

Preferably the mouthpiece is rotatably movable between the storage position and the dispensing position. Alternatively the mouthpiece is pivotally movable between the storage position and the dispensing position.

Preferably the inhalation device additionally comprises a monitor for monitoring the breath of a patient.

According to one embodiment of the invention said monitor comprises one or more sensors for sensing the pressure profile associated with the breath cycle.

According to another embodiment of the invention said monitor comprises one or more sensors for sensing the airflow profile associated with the breath cycle.

According to another embodiment of the invention said monitor comprises one or more sensors for sensing the temperature profile associated with the breath cycle.

According to a further embodiment of the invention said monitor comprises one or more sensors for sensing the moisture profile associated with the breath cycle.

According to a further embodiment of the invention said monitor comprises one or more sensors for sensing the oxygen or carbon dioxide profile associated with the breath cycle.

Preferably said monitor sends an actuation signal to the actuator.

Preferably receipt of said actuation signal triggers release of medicament from a medicament carrier.

Preferably the collar portion additionally includes a microelectronic memory chip.

Preferably the body includes electrical contact pins. Preferably said electrical contact pins are connectable to a microelectronic system. Preferably said electronic contact pins are positioned such that they only contact the microelectronic memory chip when the actuator is in the dispensing position.

Preferably the body is additionally provided with a sensor to detect the initial movement of the actuator from the storage position.

Preferably the device is provided with a dose counter.

Preferably the device is provided with a display window.

Preferably the inhalation device additionally comprises a medicament carrier, receivable by the collar portion and the body.

Preferably the medicament carrier is insertable into the support to allow passage of medicament through the nozzle and into the mouthpiece.

Preferably the medicament carrier and actuator are reversibly loadable into the body when the actuator is positioned midway between the storage and dispensing positions.

Preferably the medicament carrier is an aerosol container.

Preferably said aerosol container comprises a suspension of a medicament in a propellant.

Preferably said propellant comprises liquefied HFA134a, HFA-227 or carbon dioxide.

Preferably the medicament is selected from the group consisting of albuterol, salmeterol, fluticasone propionate and beclomethasone dipropionate and salts or solvates thereof and any mixtures thereof.

Preferably the medicament comprises salmeterol xinafoate and salts or solvates thereof and any mixtures thereof. More preferably the medicament comprises fluticasone propionate and salts or solvates thereof and any mixtures thereof. More preferably the medicament comprises a combination of salmeterol xinafoate and fluticasone propionate and salts or solvates thereof and any mixtures thereof.

Preferably said body is shaped to be holdable in one hand and the mouthpiece is movable from its storage position to its dispensing position by a motion of the thumb on the same hand.

Preferably at least a portion of the mouthpiece is shaped for ease of grip by the user.

In one aspect of the present invention there is also provided the use of an inhalation device for dispensing medicament According to one embodiment there is also provided a kit of parts comprising a body, the body being shaped for receipt of a medicament carrier and having an air channel therein; and an actuator having a mouthpiece, the actuator being reversibly movable between a dispensing position and a storage position, the actuator including an air hole; such that when assembled the air channel communicates with the air hole when the actuator is in the dispensing position and the air channel and the air hole do not communicate when the actuator is in the storage position.

The kit of parts may additionally comprise an aerosol container for containing medicament.

BRIEF DESCRIPTION OF THE DRAWINGS

The invention will now be described with reference to the accompanying drawings in which:

FIG. 1 shows a perspective sectional view of an actuator and mouthpiece of an inhalation device according to the present invention.

FIG. 2 shows a perspective view of a portion of a body according to the present invention.

FIGS. 3*a* and 3*b* show sectional views of the actuator and body of FIGS. 1 and 2 with the actuator and mouthpiece in the respective dispensing and storage positions.

FIG. 4 shows a sectional view of an inhalation device herein with the mouthpiece in the storage position.

FIGS. 5*a* and 5*b* show perspective views of an aerosol container with a collar attached.

DETAILED DESCRIPTION OF THE DRAWINGS

FIG. 1 shows an actuator 10 for use in an inhalation device comprising a collar portion 5; mouthpiece 20; stem block 30; and a passage defining a nozzle 40. The collar portion 5 is separated from the mouthpiece by solid base portion 12. The stem block 30 provides a support for the dispensing end of a medicament container such as a valve stem of an aerosol container (not shown) and nozzle 40 allows for passage of the contents of the aerosol container into the mouthpiece for subsequent inhalation by the patient through the mouthpiece 20. The solid base portion 12 prevents air from entering the collar 10 and subsequently the body of the device (not shown), therefore preventing moisture from containing any moisture sensitive apparatus located within the body. The mouthpiece 20 has air holes 25 (only one shown) located in the non-dispensing end 22. The air holes 25 communicate with air channel located in the body (not shown) to provide an air path.

FIG. 2 shows a portion of the body 150. The body 150 has a hole 151 shaped to receive the collar of the actuator of FIG. 1 and a portion 152 shaped to fit with the mouthpiece of the actuator of FIG. 1. The actuator (not shown) may be inserted into the body 150 so that the collar is located in hole 151 and the mouthpiece lies against the portion 152 when it is in the storage position. End cap 154 covers the dispensing end of the mouthpiece, protecting it from ingress of contaminants. The body portion 152 contains a number of air channels 153 which are arranged in a finger pattern and pass through the surface of the body 150. The finger arrangement has been found to allow for a high level of air movement through the body 150, however the air channels 153 may be arranged in other formations, for example in a series of lines or grooves, or in another suitable pattern.

FIG. 3*a* shows the actuator and body of FIGS. 1 and 2 in position with the mouthpiece 220 located in the storage position. The figure has been simplified to show only the actuator, a body 250 and aerosol container 280. The aerosol container 280 is inserted in the stem support 230, blocking airflow between the mouthpiece 220 and the collar portion 205. The solid base portion 212 of the collar portion 205 prevents airflow between the mouthpiece 220 and the rest of the inhalation device. The mouthpiece 220 is covered by end cap 254 of the body 250, preventing ingress of contaminants during storage. The air holes 225 (only one shown) in the mouthpiece 220 are blocked by the body 250 and the air channels 253 in the body 250 are blocked by the mouthpiece 220. There is therefore no communication between the body and the mouthpiece during storage. Also shown is microelectronic memory chip 260 located next to the aerosol container 280 and electrical contact pins 262 located within the body 250. In the storage position, the microelectronic memory chip 260 does not make electrical contact with the contact pins 262.

FIG. 3*b* shows the device of FIG. 3*a* with the mouthpiece located in the dispensing position. The aerosol container 280 is inserted in the stem support and will release medicament through the nozzle 240 into the mouthpiece 220 for inhalation by the patient. The solid base portion 212 of the collar portion 205 prevents air from entering the rest of the device when the patient breathes into the mouthpiece 220. The air hole 225 in the mouthpiece 220 is aligned with the air channels 253 in the body 250, allowing in-use circulation of air and creating airflow through the mouthpiece 220. The microelectronic memory chip 260 located next to the aerosol container 280 and the electrical contact pins 262 in the body are aligned when the mouthpiece is in the dispensing position such that electrical contact is made.

FIG. 4 shows a metered dose inhaler for the delivery of medicament for inhalation by a patient. The inhaler comprises a housing body 350 in which an aerosol container 380 is located. An actuator in the form of a mouthpiece 320 is provided to the aerosol container 380.

The aerosol container 380 has a valve dispensing mechanism 382 in the form of a slide valve. Valve stem 384 connects with a stem support 330 which forms part of the actuator 310. The support 330 is provided with an outlet passage 340 enabling dispensed dose to pass through to the mouthpiece outlet 321. It will be appreciated that dispensing of the dose requires the aerosol container 380 to be depressed to actuate the slide valve dispensing mechanism 382 and dispense medicament into the outlet 321 from which it can be inhaled by a patient.

The actuator 310 has a tubular neck portion 305 for receipt of a collar 336 which itself engages the neck of the aerosol container 380. The tubular portion 305 is shaped such that collar 336 and so-engaged aerosol container are sufficiently movable in a sliding fashion therein to enable actuation of the slide valve mechanism 382. The aerosol container 380, collar 336 and actuator 310 together from a discrete unit which is reversibly removable from the body 350 when the actuator 310 is in certain orientations. The drawing shows the actuator in the endpiece secured orientation in which retaining lip 308 makes snap-fit engagement with groom 338 provided in the tubular portion 305 of the actuator. A perpendicular opposing point (i.e. 90° rotation therefrom) on the tubular portion 305 has no similar groove portion, such that when the actuator 310 is rotated through 90° to the endpiece unsecured orientation the actuator 310, collar 336 and aerosol container may be removed from the housing body 350.

The mouthpiece 320 is separated from the tubular collar 305 by solid base portion 312. The solid base portion 312 prevents air from entering the collar 305 and the interior of the device, therefore preventing moisture from contacting any moisture sensitive apparatus located therewithin. The mouthpiece 320 has air bolts 325 (only one shown) located in the non-dispensing end 322. In the dispensing position, the air holes 325 communicate with air conduits 353 located in the body 350 to provide an air path. In the storage (i.e. 'endpiece unsecured') position, it will be appreciated that the air holes 325 do not communicate with the air conduits 353.

The collar 336 is provided with an electronic memory chip 360 which is capable of receiving data inputs and providing data outputs. The memory chip 360 connects via contact 362 to electronic circuitry (not visible) and power supply in the form of two lithium batteries 362*a* and 363*b*. The electronic circuitry further connects to electronic control system 370 which is capable of communication with the memory chip 360 and with various sensors on device (for simplicity, not shown) and of providing visual output via display 374 to the patient.

It may be seen that the upper part of the aerosol container 380 is received by container seat 355. The container seat 355 is slidably movable within the housing along track 356 formed within the housing 350. The container seat 355 also comprises a spring actuator return 357 and actuator button 376 for use as a manual override. Plural lengths of shape memory alloy wire 372*a*, 372*b* (only two wires shown for simplicity) connect the container seat 355 to anchor positions 359*a*, 359*b* in the lower part of the housing. The wires 372*a*, 372*b* comprise a nickel-titanium alloy which contracts in response to the heating effect of the flow of electrical current therethrough. It may thus, be appreciated that when electrical current is passed through the plural lengths of wire 372*a*, 372*b* the container seat 355 will be drawn towards to the anchor positions 359*a*, 359*b* as the wires 372*a*, 372*b* contract. Actuation of the valve dispensing mechanism 382 and dispensing of medicament dose will thereby result. The flow of electrical current is controlled by the control system 370, which is itself responsive to inputs from various sensors (not shown) such as a sensor which senses the breath of a patient.

In the event of failure of electrical current flow it may be appreciated that the manual actuation button 376 may be manually pushed downwards to actuate the valve dispensing mechanism 382. The actuation step also results in the closing of switch 376 which records that a dose has been fired.

Figure 2:
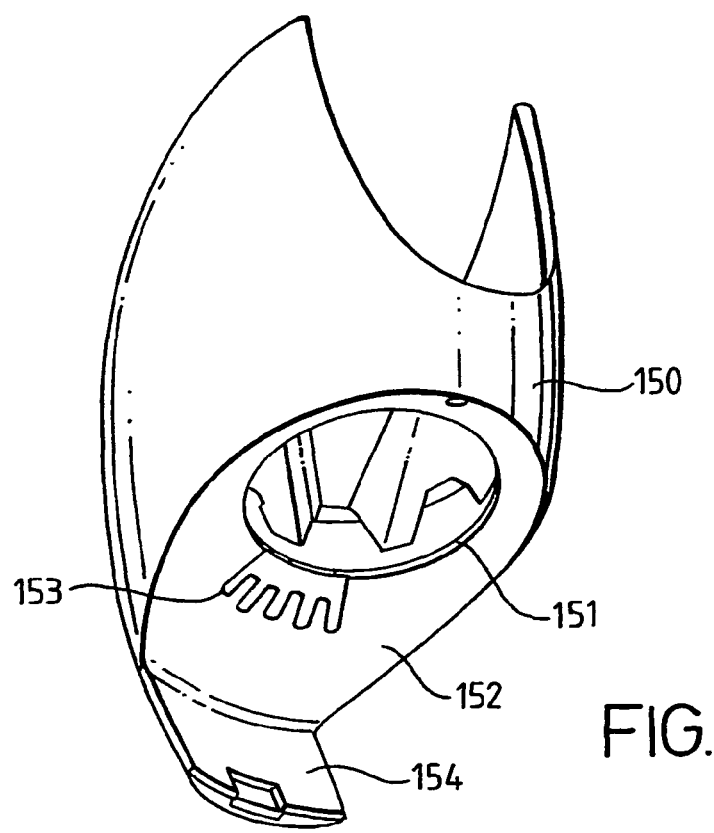
Figure 3A:
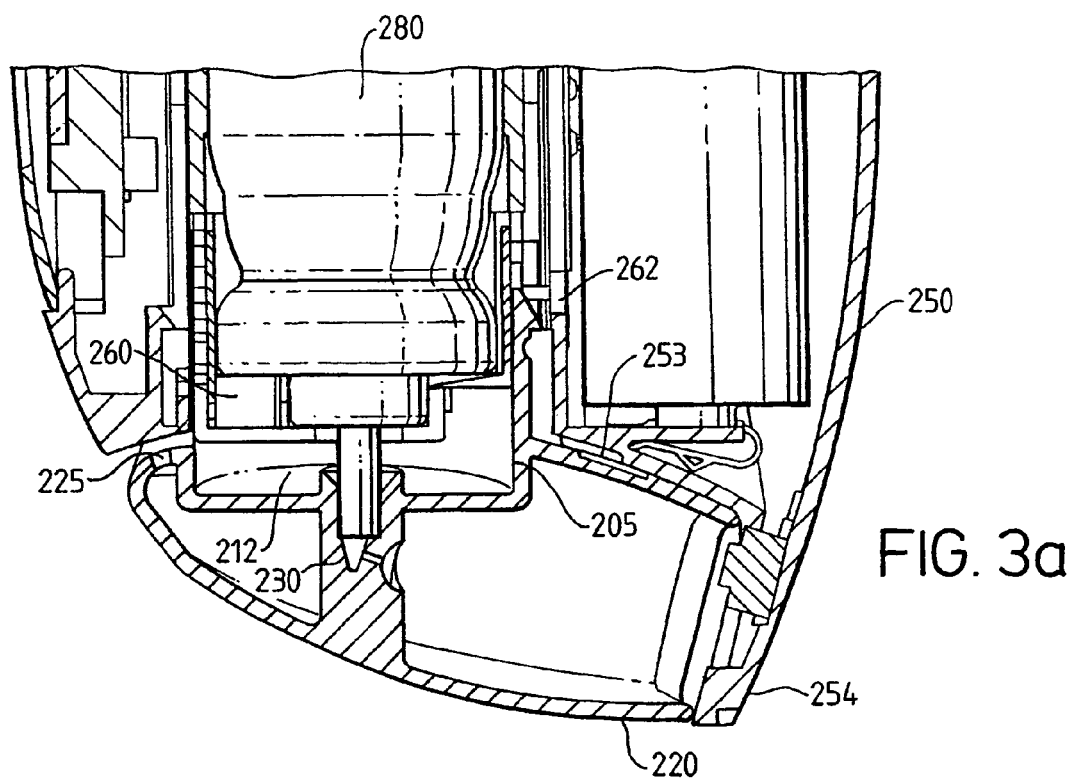
Figure 3B:
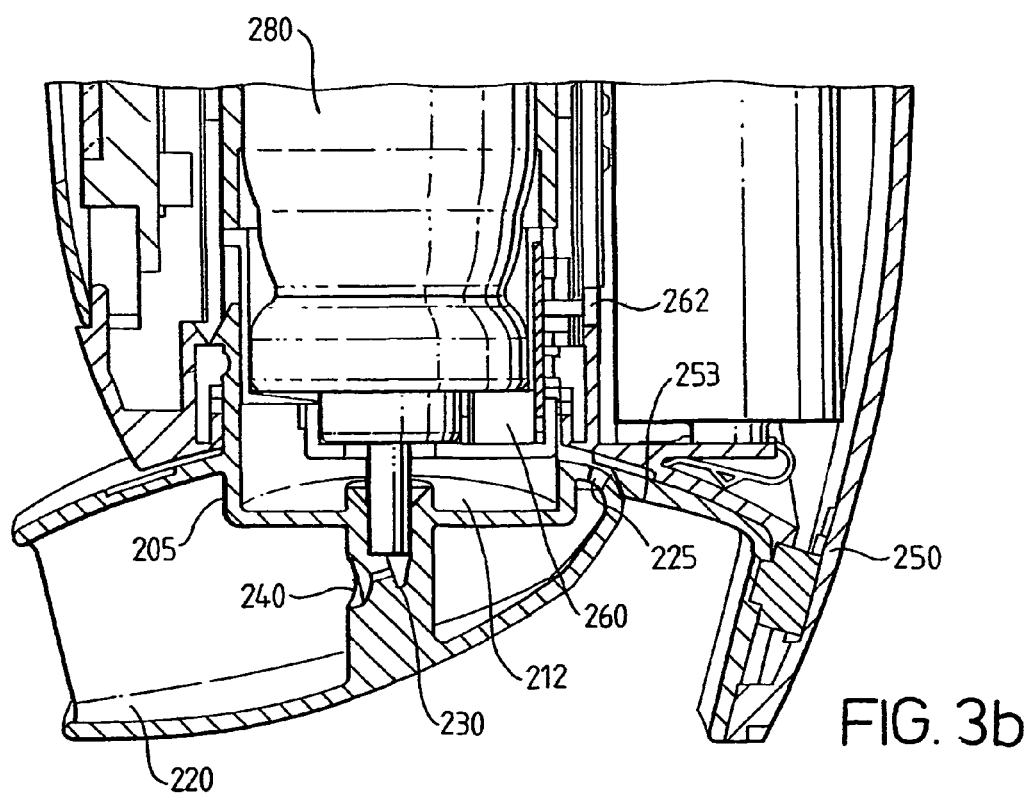
Figure 4:
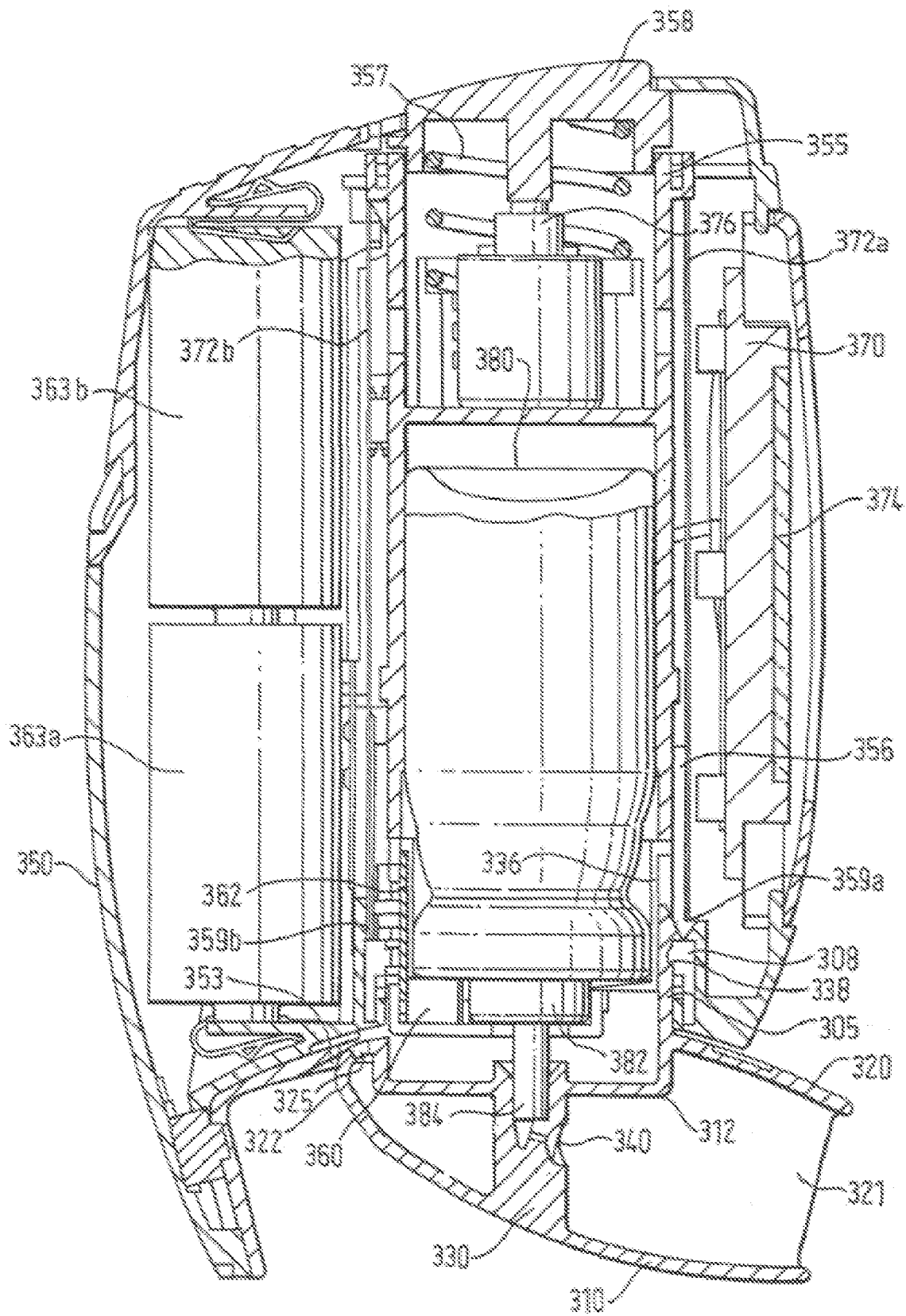
Figure 5A:
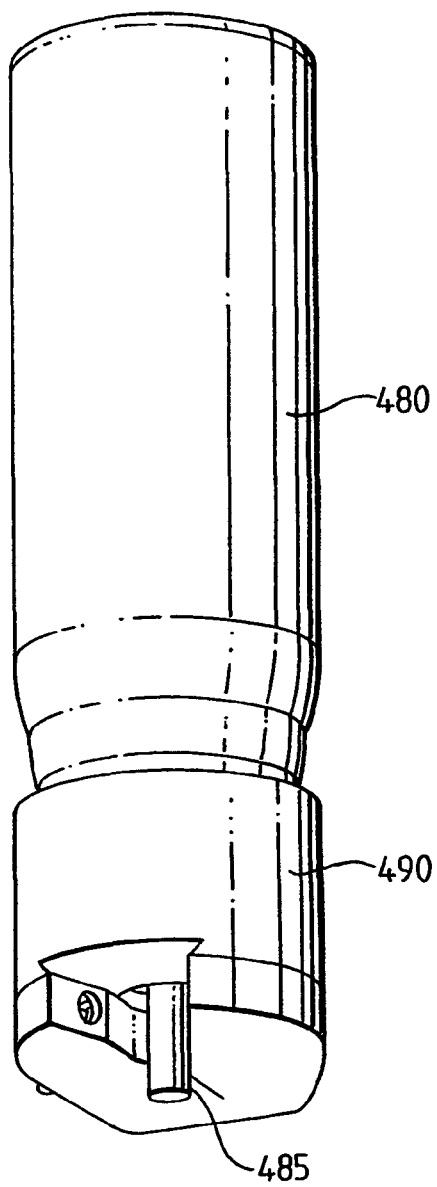
Figure 5B:
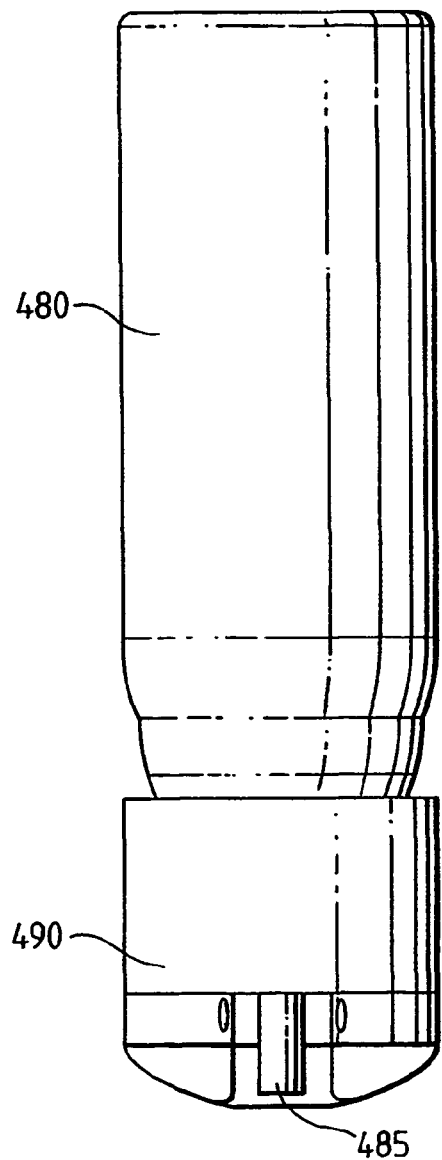

FIGS. 5*a* and 5*b* show aerosol container 480 with a collar 490 attached. The collar 490 is fixed such that the stem 485 of the aerosol container 480 protrudes. The assembly of aerosol container 480 and collar 490 may be combined with an actuator similar to that shown in FIG. 1 and a body similar to that shown in FIG. 2 to make an assembly similar to that shown in FIGS. 3*a* and 3*b*.

The aerosol container and inhalation device of the invention is suitable for dispensing medicament, particularly for the treatment of respiratory disorders. Medicaments which may be administered in the aerosol formulations include any drug useful in inhalation therapy. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (eg as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2 (3H)-benzothiazolone; adenosine 2a agonists, eg 2R,3R,4S, 5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha_4$ integrin inhibitors eg (2S)-3-[4-({[4-(aminocarbonyl)-1-piperidinyl] carbonyl}oxy)phenyl]-2-[((2S)-4-methyl-2-{[2-(2-methylphenoxy) acetyl]amino}pentanoyl)amino]propanoic acid (e.g. as free acid or potassium salt), diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an anti-inflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. An inhalation device for dispensing medicament comprising
    a body, said body being configured to receive an aerosol container which contains a medicament and has a valve stem; and
    an actuator which is reversibly movable relative to the body between a dispensing position and a storage position, said actuator having:
    a mouthpiece for insertion into a patient's mouth, the mouthpiece having a wall structure which defines a chamber to which a dispensing opening is provided at which a patient is able to inhale and, in use of the device, create an airflow to entrain medicament dispensed by the device;
    a collar portion provided on the wall structure and having a chamber for receipt of the aerosol container; and
    a stem block for supporting the aerosol container, the stem block having a passageway which extends from an inlet opening, into which the valve stem is insertable, to an outlet opening, configured as a nozzle providing communication between the mouthpiece dispensing opening and the aerosol container;
    wherein said body includes at least one air channel, and said actuator includes at least one air hole in the wall structure such that said at least one air channel communicates with said at least one air hole when the actuator is in said dispensing position and the at least one air channel and air hole do not communicate when the actuator is in said storage position;
    wherein when the actuator is in the dispensing position the at least one air hole establishes an airflow path connecting the least one air channel to the mouthpiece dispensing opening via the mouthpiece chamber along which an airflow moves upon patient inhalation at the mouthpiece dispensing opening;
    wherein the collar portion chamber has a solid base portion which is formed by the wall structure of the mouthpiece and defines a partition between the respective chambers of the collar portion and the mouthpiece thereby providing the solid base portion with a collar portion side which forms a boundary surface of the collar portion chamber and a mouthpiece side which forms a boundary surface of the mouthpiece chamber;
    wherein the stem block is in and extends through the solid base portion such that the passageway of the stem block is in and extends through the solid base portion and the inlet opening of the stem block is located in the collar portion chamber and the outlet opening is located in the mouthpiece chamber; and
    wherein the passageway of the stem block is the only passageway in and extending through the solid base portion which provides communication between the mouthpiece and collar portion chambers.

2. An inhalation device according to claim 1 wherein either the at least one air channel or the at least one air hole is blocked when the actuator is in the storage position.

3. An inhalation device according to claim 1 wherein both the at least one air channel and the at least one air hole are blocked when the actuator is in the storage position.

4. An inhalation device according to claim 1 wherein said at least one air channel forms a slot.

5. An inhalation device according to claim 1 wherein the body has a plurality of air channels.

6. An inhalation device according to claim 5 wherein said plurality of air channels are arranged in a finger arrangement.

7. An inhalation device according to claim 1 wherein the at least one air holes is a slot.

8. An inhalation device according to claim 1 wherein the mouthpiece is covered by the body in the Storage position and protrudes from the body in the dispensing position.

9. An inhalation device according to claim 1 wherein the mouthpiece is rotatably movable between the storage position and the dispensing position.

10. An inhalation device according to claim 1 wherein the collar portion additionally includes a microelectronic memory chip.

11. An inhalation device according to claim 1 wherein the body additionally includes electrical contact pins.

12. An inhalation device according to claim 11 wherein said electrical contact pins are connectable to a microelectronic system.

13. An inhalation device according to claim 11 wherein said electrical contact pins are positioned such that they only contact the microelectronic memory chip when the actuator is in the dispensing position and do not contact the microelectronic memory chip when the actuator is in the storage position.

14. An inhalation device according to claim 1 wherein the body is additionally provided with a sensor to detect the initial movement of the actuator from the storage position.

15. An inhalation device according to claim 1 wherein the device is provided with a dose counter.

16. An inhalation device according to claim 1 wherein the device is provided with a display window.

17. An inhalation device according to claim 1 additionally comprising an aerosol container which contains medicament, receivable by the collar portion and the body.

18. An inhalation device according to claim 17 wherein said aerosol container comprises a suspension of medicament in a propellant.

19. An inhalation device according to claim 17 wherein the medicament is selected from the group consisting of albuterol, salmeterol, fluticasone propionate and beclomethasone dipropionate and salts or solvates thereof and any mixtures thereof.

20. An inhalation device according to claim 19, wherein said medicament comprises salmeterol xinafoate.

21. An inhalation device according to claim 19, wherein the medicament comprises fluticasone propionate.

22. An inhalation device according to claim 19, wherein the medicament comprises a combination of salmeterol xinafoate and fluticasone propionate.

23. An inhalation device according to claim 1 wherein the aerosol container and actuator are reversibly loadable into the body when the actuator is positioned midway between the storage and dispensing position.

24. An inhalation device according to claim 1 wherein the body is shaped to be holdable in one hand and the actuator is movable from its storage position to its dispensing position by a motion of the thumb on the same hand.

25. An inhalation device according to claim 1 wherein at least a portion of the mouthpiece is shaped for ease of grip by the user.

* * * * *

UNITED STATES PATENT AND TRADEMARK OFFICE
CERTIFICATE OF CORRECTION

PATENT NO.        : 7,383,837 B2
APPLICATION NO.   : 10/362699
DATED             : June 10, 2008
INVENTOR(S)       : Robertson et al.

It is certified that error appears in the above-identified patent and that said Letters Patent is hereby corrected as shown below:

On the cover page, item

[*] Notice:   Subject to any disclaimer, the term of this patent is extended or adjusted under 35 USC 154(b) by (95) days Delete the phrase "by 95 days" and insert -- by 108 days --

Signed and Sealed this

Ninth Day of June, 2009

JOHN DOLL
*Acting Director of the United States Patent and Trademark Office*